US009579312B2

(12) United States Patent
Minowada

(10) Patent No.: US 9,579,312 B2
(45) Date of Patent: Feb. 28, 2017

(54) METHOD FOR TREATING/PREVENTING DISEASE USING COGNITIVE ABILITY OF CEREBRUM AND PHARMACEUTICAL

(71) Applicant: SYSTEM C, Sakyo-ku, Kyoto-shi (JP)

(72) Inventor: Takuro Minowada, Sakyo-ku (JP)

(73) Assignee: SYSTEM C, Kyoto-shi (JP)

( * ) Notice: Subject to any disclaimer, the term of this patent is extended or adjusted under 35 U.S.C. 154(b) by 0 days.

(21) Appl. No.: 14/788,358

(22) Filed: Jun. 30, 2015

(65) Prior Publication Data

US 2015/0320735 A1    Nov. 12, 2015

Related U.S. Application Data

(63) Continuation of application No. 12/295,139, filed as application No. PCT/JP2006/314530 on Jul. 21, 2006, now abandoned.

(30) Foreign Application Priority Data

Mar. 29, 2006  (JP) ................................ 2006-091370

(51) Int. Cl.
| | | |
|---|---|---|
| *A61K 31/4515* | (2006.01) | |
| *A61K 31/197* | (2006.01) | |
| *A61K 31/15* | (2006.01) | |
| *A61K 9/00* | (2006.01) | |
| *A61K 9/20* | (2006.01) | |
| *A61K 31/00* | (2006.01) | |
| *A61K 31/375* | (2006.01) | |
| *A61K 31/4523* | (2006.01) | |
| *A61K 33/26* | (2006.01) | |
| *A61K 45/06* | (2006.01) | |
| *A61K 9/19* | (2006.01) | |

(52) U.S. Cl.
CPC ......... *A61K 31/4515* (2013.01); *A61K 9/0019* (2013.01); *A61K 9/0085* (2013.01); *A61K 9/2018* (2013.01); *A61K 31/00* (2013.01); *A61K 31/15* (2013.01); *A61K 31/197* (2013.01); *A61K 31/375* (2013.01); *A61K 31/4523* (2013.01); *A61K 33/26* (2013.01); *A61K 45/06* (2013.01); *A61K 9/19* (2013.01)

(58) Field of Classification Search
USPC ........................................................ 514/183
See application file for complete search history.

(56) References Cited

U.S. PATENT DOCUMENTS

| | | | | |
|---|---|---|---|---|
| 4,020,103 | A | | 4/1977 | Trocki |
| 4,085,225 | A | * | 4/1978 | Welle ............................ 514/523 |
| 5,089,276 | A | | 2/1992 | Yamashita et al. |
| 5,292,774 | A | | 3/1994 | Hiraide et al. |
| 5,837,701 | A | * | 11/1998 | Bleiweiss ............... A61K 31/00 |
| | | | | 514/217 |
| 5,993,863 | A | * | 11/1999 | Kikuchi ................ A61K 9/0029 |
| | | | | 424/602 |
| 6,433,225 | B1 | * | 8/2002 | Chitturi .................. A61K 31/15 |
| | | | | 564/256 |
| 6,482,850 | B2 | * | 11/2002 | Ali ........................ C07D 305/14 |
| | | | | 514/449 |
| 6,743,953 | B2 | | 6/2004 | Kumar T. K. et al. |
| 7,611,872 | B2 | | 11/2009 | Beck et al. |
| 2004/0072824 | A1 | | 4/2004 | Telerman et al. |
| 2008/0096926 | A1 | | 4/2008 | Kusmierek |
| 2011/0092548 | A1 | | 4/2011 | Minowada |

FOREIGN PATENT DOCUMENTS

| | | |
|---|---|---|
| JP | 9020666 | 1/1997 |
| JP | 10182471 | 7/1998 |
| JP | 2003-514857 | 4/2003 |
| JP | 2005-524601 | 8/2005 |
| JP | 2006-505589 | 2/2006 |
| WO | 01/13783 | 5/2001 |
| WO | 02/22573 | 3/2002 |
| WO | 2004/037783 | 5/2004 |

OTHER PUBLICATIONS

Masaki Okuyama et al. (Surgery Today (2005) 35:36-40).*
Ross et al. (Am Fam Physian 2001;64:807-14).*
Bram et al., "Vitamin C preferential toxicity for malignant melanoma cells," *Nature* 284:629-631, Apr. 17, 1980.
Cameron et al., "Supplemental ascorbate in the supportive treatment of cancer: Prolongation of survival times in terminal human cancer*," *Proc. Natl. Acad. Sci.* 73(10):3685-3689, Oct. 1976.
Cameron et al., "Supplemental ascorbate in the supportive treatment of cancer: Reevaluation of prolongation of survival times in terminal cancer*," *Proc. Natl. Acad. Sci.* 75(9):4538-4542, Sep. 1978.
De Cicco et al., "Supportive therapy of elderly cancer patients," *Critical Reviews in Oncology/Hematology* 42:189-211, 2002.
Greenfield, "Biotechnology, the brain and the future," *TRENDS in Biotechnology* 23(1):34-41, 2005.
González et al., "Orthomolecular Oncology Review: Ascorbic Acid and Cancer 25 Years Later," *Integrative Cancer Therapies* 4(1):32-44, 2005.
Japan Pharmaceutical Information Center, "Iryoyaku Nippon Iyakuhinshu," vol. 27th Ed., pp. 1358-1359, Oct. 25, 2003. (with English translation).
Japan Pharmaceutical Information Center, "Iryoyaku Nippon Iyakuhinshu 2004," vol. 27th Ed., pp. 2170-2171, Oct. 25, 2003. (with English translation).
Morita et al., "Drug therapy for psychiatric symptoms in cancer patients," *Igaku No Ayumi* 205(12):907-910, Jun. 21, 2003. (with English translation).
Murata et al., "Vitamin C to Kaze, Gan no Yobo," *Food Chemicals* 6(3):33-37, Mar. 1990. (with English translation).

(Continued)

*Primary Examiner* — Sabiha N Qazi

(74) *Attorney, Agent, or Firm* — Seed IP Law Group LLP

(57) ABSTRACT

An object of the present invention is to develop a method of enhancing the cognitive ability of a brain to fundamentally cure a disease. It has been found out that, by using a medicament for treating or preventing a disease including a combination of a major tranquilizer, and vitamin C or a salt thereof and, if necessary, drip infusion, an antidepressant and an iron agent, the cognitive ability of a brain is enhanced, thus, an arbitrary disease including various cancers can be treated. The present invention also provides a method for treating or preventing a disease including a step of administering a major tranquilizer, and vitamin C or a salt thereof to a subject suffering from the disease.

2 Claims, 3 Drawing Sheets

(56) References Cited

OTHER PUBLICATIONS

Nakura, "Gansei Hinketsu eno Taio," *Igaku No Ayumi* 164(5):393-397, Jan. 30, 1993. (with English translation).

Okuyama et al., "Preoperative Iron Supplementation and Intraoperative Transfusion During Colorectal Cancer Surgery," *Surg. Today* 35:36-40, 2005.

Ross et al., "Management of Common Symptoms in Terminally Ill Patients: Part I.," *American Family Physician* 64(5):807-814, Sep. 1, 2001.

Urushizaki, "Gan no Gappeisho to Sono Kanwa," *Igaku No Ayumi* 164(5):423-426, Jan. 30, 1993. (with English translation).

Voskoglou-Nomikos et al., "Clinical Predictive Value of the in Vitro Cell Line, Human Xenograft, and Mouse Allograft Preclinical Cancer Models," *Clinical Cancer Research* 9:4227-4239, Sep. 15, 2003.

Weimann et al., "Studies on wound healing: effects of calcium D-pantothenate on the migration, proliferation and protein synthesis of human dermal fibroblasts in culture," *Ing. J. Vitam. Nutr. Res.* 69(2):113-119, Mar. 1999.

\* cited by examiner

METHOD FOR TREATING/PREVENTING DISEASE USING COGNITIVE ABILITY OF CEREBRUM AND PHARMACEUTICAL

TECHNICAL FIELD

The present invention relates to a method and a medicament for treating or preventing a disease. More particularly, the present invention relates to a method and a medicament for treating or preventing a disease using cognition of the cerebrum.

BACKGROUND ART (Structure of Brain)

A structure of a brain is said to be most mysterious in this universe. A human brain is classified into cerebrum and cerebellum. Simply speaking, cerebrum is a part which controls the psychiatric function, and cerebellum is a part which controls balance sense. When these two are compared, the weight of cerebellum is around 11% of a whole brain, and cerebrum accounts for a major part. When a longitudinal cross-section of a brain is observed, in the center, there are diencephalon, mesencephalon, and medulla oblongata, and medulla oblongata which is continuous with spinal cord.

(Is a Brain Heavy?!)

To say a weight of a whole brain, it is about 1450 gram in men, and is about 1300 gram, a little bit lighter in women. Does the difference in the brain weight mean that women are less wise than men? The answer is no. It has been known that wisdom does not depend on the brain weight. Meanwhile, there is a concern that if a person having such a heavy head at the top of the body has such a heavy thing placed on the head, this person might have stiff shoulders, but this is not true. A brain is protected with a triple membrane consisting of dura mater, arachnoid mater and pia mater in this order from the outside, and an about one cup of spinal fluid is filled between the arachnoid mater and the pia mater. By walking upright with two feet, a brain is supported by a spinal column which is in an appropriately vertical position, and an actual brain weight is not felt.

(Wrinkle of Brain)

If it is concluded that a weight of a brain has no relationship with the wisdom, what is related to the wisdom? As is frequently said from old times, there is another opinion that a person whose brain has many wrinkles is wise. A human brain has, if getting rid of wrinkles, a 2250 square centimeter area, that is, a size of one side of a newspaper. It can also be said that the wrinkles had to be folded and stored without a choice to place such a large-size brain into a narrow skull bone.

Therefore, it can be said that a wrinkle indicates a folding part. Two thirds of a surface area of a human brain is hidden in a groove of this wrinkle, and can not be seen from the outside. What can be said regarding a wrinkle is only that the relationship between a surface area when wrinkles of the brain is removed and a size of a container for a brain determines the number of wrinkles.

(Network of Nerve Cell)

When it is concluded, as described above, that neither a weight nor a wrinkle is related to the wisdom, what is a determinant factor? A possible answer is the number and the function of brain nerve cells. Meanwhile, the number of nerve cells of a human brain is said to be 14 billion in total, and when were a total of 14 billion nerve cells generated? Surprisingly, it is known that 14 billion nerve cells have already been generated at birth, same as in an adult, all equally.

In principle, a nerve cell is not divided. Assuming that there are a total of 14 billion nerve cells, all of the 14 billion nerve cells seem to be necessary for the balance or stabilization in a skull bone. Dr. Takeshi Yoro (former professor of the Institute of Brain Research, the University of Tokyo) reported that, even when a certain part of nerve cells injured, a human can live a normal life with only 3% of nerve cells. It is also reported that, even when a certain part gets damaged, intact neurons replace for it over a long time.

When a shape of a nerve cell is seen, many prickle-like materials are projected from a nerve cell. Normally, there are a few tens of prickles, and only one long prickle among them is called nerve fiber. It is shaped like a connected Vienna sausages and has a bulging part at the end. This is called terminal button. The button attaches to a adjacent or peripheral nerve cell. They are not fused into each other but merely lapped and adhered. The more binding formats there are, the better results occur, that is, a brain in which larger number of this network of nerve cells is generated more closely results in the wisdom.

(Formation of Network)

Entanglement of the nerve cells grows frequently three months after birth. It is said that, at 15 months, the entanglement becomes more complicated and, at about 3 years old to 4 years old, the development of a fundamental network is completed. A size of a brain becomes about 4-fold bigger at around 4 year old than at birth, approximately the same size as an adult. For this reason, the environment in childhood is important.

(Team Work of Brain)

A human memorizes many things every day. It is said that a brain has 14 billion nerve cells, and in which part of a brain the memorization is performed becomes a question. It has been known that memorization is performed in a head front (frontal cortex) which is present at a font part of a head, and in this part, the human behaviors such as creating a thing or thinking is conducted. In addition, a vertex of a head has relationship mainly with movement, and a side part of a head is responsible for memory, judgment, acoustic sense, and language. A rear part of a head controls an eye just situated on the other side of the head (visual sense). Like this, each part of cerebrum works separately. This separate work is not performed disorderly, but each part helps each other, and co-operates, thus, an organization play is conducted considerably well. For this reason, when a separate working system is well established, the brain works well (FIG. 1).

(Nerve Cells of a Brain are Decreasing)

Sixty to eighty thousand nerve cells of a brain are dying every day, and as a human is getting older, the number of destroyed nerve cells is increased. Since the nerve cell is not regenerated, nerve cells are decreasing without stopping. From the age of about 40, the decrease becomes remarkable. It is said that, from calculation, the nerve cell becomes zero at the age of 230. It is said that 200 thousand cells are lost every day around the age of over 40, and the number of lost cells becomes about 73 million per year. However, this seems trivial.

Japanese psychiatric medicine is directed to psychiatric analytical methodology too much, and is substantially delayed in study involving the function and the structure of cerebrum or positioning of those psychiatric medicines in the clinic setting. From now on, such region must be studied more vigorously. Now, let's discuss on the function of a brain by exemplifying an easily understandable example.

We see objects or the surrounding situation through eyes every day, but we don't always actually "see" all things that meet eyes. When we see a face of a person, even if there is a vase behind the person, we do not "see" the vase.

However, it is not considered that such the selection is conducted by the central function of visual sense.

Alternatively, when we are chatting with a person, accompanying a content of a conversation, past memory is recalled, or new presumption or imagination is generated. In such a case, no one think that such association is generated in a center of an acoustic sense.

Like this, concentration in something, recall of a memory, and imagination are not conducted in only one center such as a center of a visual sense, a center of an acoustic sense, and a center of memory. Thinking from such a thing, it is important to not only analyze each individual center separately but also comprehensively study the whole cerebrum which controls them (FIG. 2).

Meanwhile, since around 1980 in Europe and USA, a concept called Solution Focused Approach has been developed (FIG. 6).

This is a way of thinking that "it is important to treat an affected part and, at the same time, maintain a healthy part immediately."

This approach has been previously adopted mainly in department of psychosomatic medicine although ambiguously, and is a thinking way that, to treat the diseases that are not clearly grasped when pursued by a 20-century diagnosing method with poor laboratory data such as autonomic ataxia and physical abnormality, it is important to recognize and make use of the intact functions immediately rather than to detect and care the injured functions.

In such a sense, this approach is going against the scientific methodology involving mainly analysis, which is peculiar to previous Westerner (Mr. Wilder Penfield (Canada) proposed an analytical procedure, while Mr. Karl Lashley (Britain) proposed a non-analytical holonic procedure).

Recently, a trend of adoption of the solution focusing approach is prevailing also in a brain area to review the function of cerebrum and brain anatomical cell structure.

This is the approach to improve functions by preventing further expansion of a damaged part and maintaining an intact part, a much larger region than the damaged part.

As such, it goes without saying that initial therapy is important. However, there is a fact that, in most cases, initial therapy, which is naturally conducted in other departments, is not conducted in the department of psychiatry.

When "Solution Focusing Approach" is applied to cerebrum study, it is considered more important to consider whole cerebrum comprehensively rather than to center on a partial function center of cerebrum as previously preferred. A whole is not necessarily a sum of parts (holonic). It is thought that a whole is a whole, and only when a balance is taken as a whole and safety is confirmed, a higher order center of cerebrum works (FIG. 3).

A thinking way that a whole is more important than a part in cerebrum study was derived as a result of detailed experiment in a monkey in 1920's to 40's (Karl Lashley (Britain)).

At that time, the finding of more analytical method by Wilder Penfield of Canada was a master stream among such ways of thinking, and the Karl's method cannot be a master stream. However, it was gradually spread worldwide, and in 1981, Roger Sperry (1922-1994) who is a psychobiologist of USA received a Nobel Prize for study of the function in left and right hemispheres of cerebrum. The previous science technique to analyze more details limit to studies showing that "a center of a visual sense is present in $17^{th}$, $18^{th}$ and $19^{th}$ of lobus occipitalis," and similar findings, and an idea such as the function of a right/left brain and a whole brain has not come out.

If the cerebrum function is greatly involved in a psychiatric disease, and a disorder of the cerebrum function is deeply involved therein, it is considered that a method to treat a psychiatric disease becomes clearer by checking the cerebrum function.

For example, focusing on senile dementia which is currently increasing, a specific method will be discussed.

When any sign of dementia is suspected, the person first admits to the hospital for examinations. This is a process that was not present in the previous psychiatric hospital. In examinations, a new system with standardized checking items, not depending on subjective evaluation by a counselor is adopted, and the person's condition is precisely grasped. Depending on a degree of progression, a treating method is determined. Fundamentally, a diseased part of cerebrum is suppressed and an intact part is maintained by drug therapy to recover a decreased ability to the original state.

The concept is very simple. When an affected part comes out, it should be detected and suppressed as early as possible, and an intact part should be maintained so that the person can live a rosy later life. Of course, now to live depends on endeavor and device of each person.

For a vivid independent later life, in view of medical methodology, it is recommended that when any risk or sign of dementia is pointed out, the person should admit to the hospital for examinations to receive appropriate treatment as early as possible.

As tuberculosis and Hansen's disease, which were Previously a refractory disease, became curable by initial therapy by a physician who knows a whole, it is thought that such a time has come when a psychiatric disease is also converted into "evidence-based medicine" by introducing initial medicine mainly including drug therapy focusing on the cerebrum function as its basis (hospitalization for examinations→Solution Focused Approach etc.) (FIG. 4).

There is no doubt that cerebrum is deeply involved in a psychiatric disease, but in other physical diseases, the cerebrum function can not be neglected. It has been known also from clinical experience of the present inventor for more than 40 years that many diseases improve further by treatment on cerebrum together with local therapy.

It is thought that insulin therapy for diabetes and a cholesterol-suppressing agent for obesity are all involved in dysfunction of cerebrum, and it is natural to consider that problems such as increased CRK and dementia arises in particular occur more frequently from now on in a context with a brain.

Further, as shown in the present invention, it becomes apparent that even a cancer can be cured by treating cerebrum. It goes without saying that I, as a physician, hope, more people to know this finding.

As a conclusion, the present inventor thinks that, regardless of the type of disease, the function of cerebrum integrating mind and body must be paid more attention to treat the disease. This is because, to say extremely, all information of a body is inputted in a brain. In addition, psychological matters including past, present, imagination and others are all together inputted into cerebrum. Furthermore, natural phenomenon during the years is memorized in a brain. Since cerebrum controls a body based on the natural phenomenon recognizing that safety assured, the function of cerebrum has to be sufficiently maintained above all.

In an elderly has concomitant diseases, it is necessary to treat him/her by checking the peripheral part of a brain first. If a weight is always put on a local site which is not so important, this may conversely result in exacerbation of the state of the whole body.

A whole and a part are both important. It is thought that the scientific methodology in the 20$^{th}$ century focusing on a part is changing to the scientific approach focusing on a whole and further emphasizing relationship between a whole and a part in the 21$^{st}$ century.

It is thought that representative diseases addressed in such a change are psychiatric disease and malignant tumor. On the other hand, it is presumed that, as a theme in the medical field from now on, elucidation of a gene will be greatly closed up without any doubt.

With respect to "human genome plan" for which study and development have been rapidly progressed since 1990's, that is, a gene issue, in our country, only partial study of a DNA is marginally getting going, and control of its whole is substantially delayed. It is thought that application of gene technology in treating diseases in this area must be vigorously conducted starting from fundamental study.

Medicine to secure the healthy mind and body as early as possible, focusing on the cerebrum. The present inventor thinks that it is duty of a healthcare practitioner from now on to grasp the condition precisely and improve the damaged ability by "new medicine focusing on a whole body and maintaining a healthy part", not by "modern medicine focusing on a part."

If a normal life becomes difficult, and a person begins to suspect that he or she is ill, it is natural that he or she needs a reliable physician who can cure it. Familial care is most appreciate and only a family may be empathetic, but it goes without saying that, in order to fundamentally solve a problem, a reliable physician and reliable therapy are essential above all.

However, change in medical education, overfocus on cultivation of physicians who can see only a part, and confusion between medicine and welfare greatly destruct the clinical field of medicine.

In 17$^{th}$ century, Descartes advanced the theory that mind and body are separate. Since then, the Mind and Body Dualism has been ever governed the medical field. However, medicine of 21$^{st}$ century must be changed in a way of putting importance on a whole instead of a part. In other words, it is felt that a time has come to think again what relation is present between a brain, a body and a mind constituting a human.

Now, when this fundamental conversion is urged, attendance of conational physicians and nurses is desired towards to construction of "true medicine."

On the other hand, from accumulation of study of a brain and treatment experience on a brain, it has been known that the cerebrum function is greatly involved also in a cancer.

All information of a body is inputted in cerebrum. Cerebrum also has the function of cognizing abnormality when present anywhere. Cerebrum controls a whole body while maintaining safety of a body.

When "onset of cancer", an abnormality of a body occurs, cerebrum cognizes it and tries to exclude a cancer cell.

Then, one may have a question that "why a cancer develops in human". The reason is that when the cognitive ability of cerebrum is reduced by any reason, abnormality can not be found, permitting proliferation of a cancer cell.

Therefore, it is concluded that, in order to basically suppress a cancer, the cognizing ability of cerebrum should be activated.

Studies up to date showed that a human normally uses only 3% of cerebrum, and even when the cognitive ability is reduced, a resting 97% intact part is maintained and the cognitive ability can be enhanced again.

According to the present invention, in brief, when health of a brain can be maintained, the risk of getting a cancer is negligible. Moreover, the present inventor has explained many actual cases where a cancer patient who received treatment of cerebrum using a tranquilizer showed a recovery tendency.

Further, it has been known that even when a cancer has entered a stage of proliferation/metastasis, intake of vitamin C may suppress the proliferation. The cancer cell-proliferation-preventing effect by vitamin C is also shown in study of Dr. Linus Pauling who was rewarded a Novel prize.

The present inventor itself suffered from large intestine cancer. After being discharged from hospital, the inventor has been on a tranquilizer and vitamin C. In a health check thereafter, proliferation and metastasis were not seen at all, and a cancer specialist was surprised at it.

Additionally, when one suffers from a disease, only a family is reliable. Although there is a term of regional medicine, one can be taken care only by a family. However, a family can provide a care but not treatment. Of course, one desires to find a reliable physician who can really cure itself.

The present inventor itself is a physician who experienced a major disease, and ardently felt the necessity of a reliable physician who performs "evidence-based medicine" like the present invention.

Dr. Greenfield describes a brain and a disease in Non-Patent Literature 1 (Trends Biotechnol. 2005 January; 23(1): 34-41). However, the Literature does not describe and suggest treatment of other diseases such as cancer utilizing the cognitive ability of a brain.

Non-Patent Literature 1

Trends Biotechnol. 2005 January; 23(1): 34-41.

DISCLOSURE OF THE INVENTION

Problems to be Solved by the Invention

An object of the present invention is to develop a method of enhancing the cognitive ability of a brain to fundamentally cure a disease.

Means for Solving the Problems

The above object was attained by the present invention, in which administration of vitamin C and a major tranquilizer increased the cognitive ability of a brain, leading to cure of a disease. Therefore, the present invention provides an evidence-based therapy (FIG. 6).

Accordingly, the present invention provides the following:
(1) A medicament for treating or preventing a disease, comprising a combination of a major tranquilizer, and vitamin C or a salt thereof.
(2) The medicament according to item 1, wherein the major tranquilizer is selected from the group consisting of a butyrophenone derivative, a phenothiazine derivative and a benzamide derivative.

(3) The medicament according to item 1, wherein the major tranquilizer is a butyrophenone derivative, and the butyrophenone derivative is selected from the group consisting of haloperidol, spiperone and timiperone.
(4) The medicament according to item 1, wherein the major tranquilizer is haloperidol.
(5) The medicament according to item 1, wherein the major tranquilizer is administered at a half dose of treatment of a psychiatric disease.
(6) The medicament according to item 1, wherein the major tranquilizer is administered at a daily dose of 0.25 mg to 1 mg in terms of haloperidol.
(7) The medicament according to item 1, wherein the vitamin C is ascorbic acid which is an artificial substance.
(8) The medicament according to item 1, wherein the vitamin. C is contained so that it is administered at a daily dose of 600 mg to 1800 mg as an effective amount.
(9) The medicament according to item. 1, further combined with drip infusion.
(10) The medicament according to item 1, wherein the drip infusion is a physiological buffer containing maltose.
(11) The medicament according to item 1, wherein the drip infusion is an Ardofed injection solution.
(12) The medicament according to item 1, further combined with an antidepressant.
(13) The medicament according to item 10, wherein the antidepressant is administered when blood potassium is decreased.
(14) The medicament according to item 10, wherein the antidepressant contains fluvoxamine maleate.
(15) The medicament according to item 10, wherein the antidepressant is administered daily.
(16) The medicament according to item 1, further combined with an iron agent.
(17) The medicament according to item 12, wherein the iron agent comprises sodium ferrous citrate.
(18) The medicament according to item 9, wherein the drip infusion is administered until appetite is worked up.
(19) The medicament according to item 1, wherein the major tranquilizer is administered before bedtime.
(20) The medicament according to item 1, further combined with drip infusion and an antidepressant.
(21) The medicament according to item 1, further combined with drip infusion and an iron agent.
(22) The medicament according to item 1, further combined with drip infusion, an antidepressant and an iron agent.
(23) The medicament according to item 1, wherein the vitamin C is further combined with pantothenic acid or a salt thereof.
(24) The medicament according to item 1, wherein the disease includes at least one disease other than a psychiatric disease.
(25) The medicament according to item 1, wherein the disease includes a disease selected from the group consisting of cancer, muscular dystrophy and Huntington's chorea.
(26) The medicament according to item 10, wherein the cancer is selected from large intestine cancer, colon cancer, rectum cancer, thyroid cancer, esophagus cancer, chorionic cancer, gallbladder cancer, neuroblastoma, maxillary cancer, oral cavity cancer, genitourinary cancer, malignant lymphoma, liver cancer, prostate cancer, lung cancer, lung cell cancer, breast cancer, stomach cancer, bladder cancer, pancreas, cancer, testis cancer, uterus cancer, corpus uteri cancer, cervix uteri cancer, ovary cancer, pharynx cancer, myelocytic leukemia, brain edema, biliary cancer, neuroblasto tumor, melanocytoma, gastrinoma, insulinoma, carcinoid, kidney cancer, testicle cancer, adult T cell leukemia, vagina cancer, vulva cancer, skin cancer, upper airway cancer, head and neck cancer, teratoma, gallbladder cancer, acute myelocytic leukemia, acute lymphatic leukemia, malignant lymphoma, sarcoma, malignant melanoma, lymphoma, lung squamous epithelium cancer and spinocerebellar degeneration.
(27) A method for treating or preventing a disease, including a step of administering a major tranquilizer, and vitamin C or a salt thereof to a subject suffering from the disease.
(28) The method according to item 27, further including a step of giving drip infusion to the subject.
(29) The method according to item 27 or 28, further including a step of administering an antidepressant to the subject when blood potassium of the subject is reduced.
(30) The method according to anyone of items 27 to 29, further including a step of administering an iron agent to the subject when the subject has anemia.
(31) Use of a combination of a major tranquilizer, vitamin C or a salt thereof in production of a medicament for treating or preventing a disease.
(32) The use according to item 31, wherein the combination further comprises drops.
(33) The use according to item 31 or 32, wherein the combination further comprises an antidepressant.
(34) The use according to any one of items 31 to 33, wherein the combination further comprises an iron agent.

Effect of the Invention

The present invention exerts such an effect that almost any diseases can be treated by a simple combination of two or more kinds of drugs which have previously been used.

According to the present invention, since a patient can receive therapy under a condition mild to the patient, the maximum treatment effect can be exerted white exhaustion of a physical strength of a patient is extremely suppressed, and an undesired side effect can be avoided.

The aforementioned object, other objects, characteristics and advantages of the present invention will become more apparent from the following detailed explanation of embodiments of the present invention with reference to the drawings.

BEST MODE FOR CARRYING OUT THE INVENTION

Figure 1:
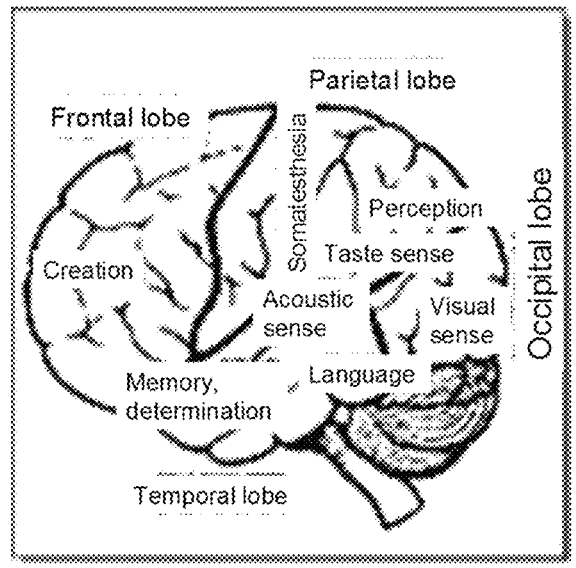
FIG. 1 is a schematic view of a brain.
Figure 2:
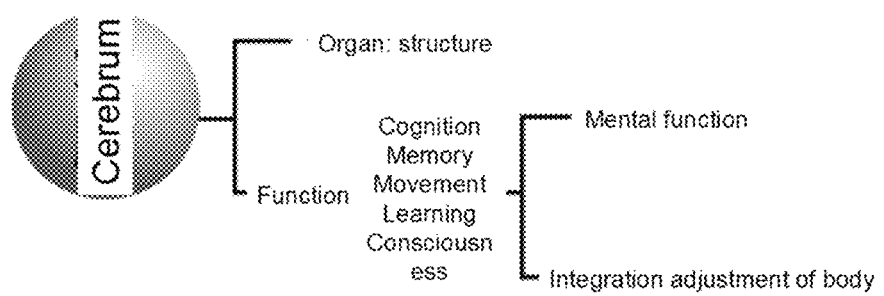
FIG. 2 is a schematic view in which structures of brain are classified.
Figure 3:
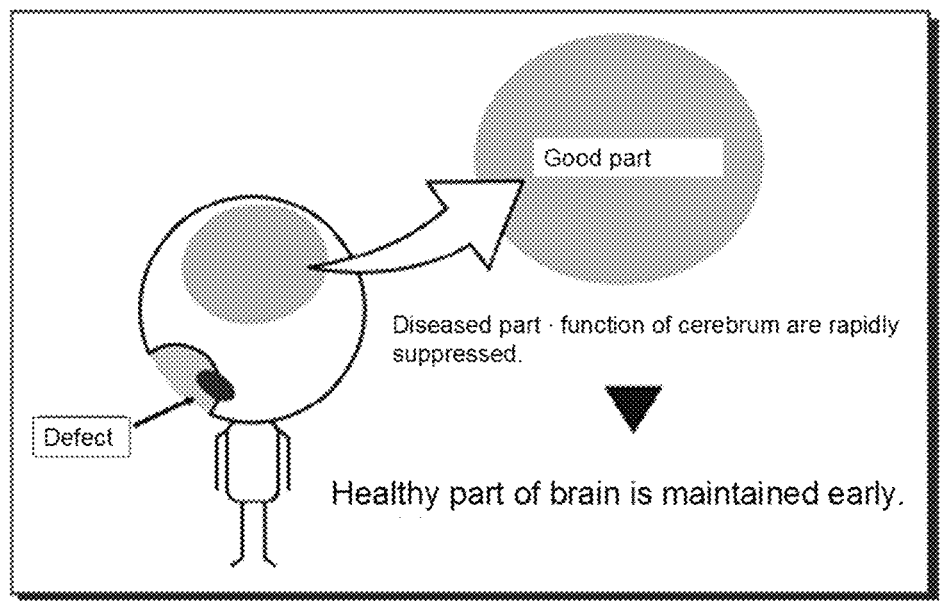
FIG. 3 is a schematic view illustrating a process in which a brain cognizes a disease.
Figure 4:
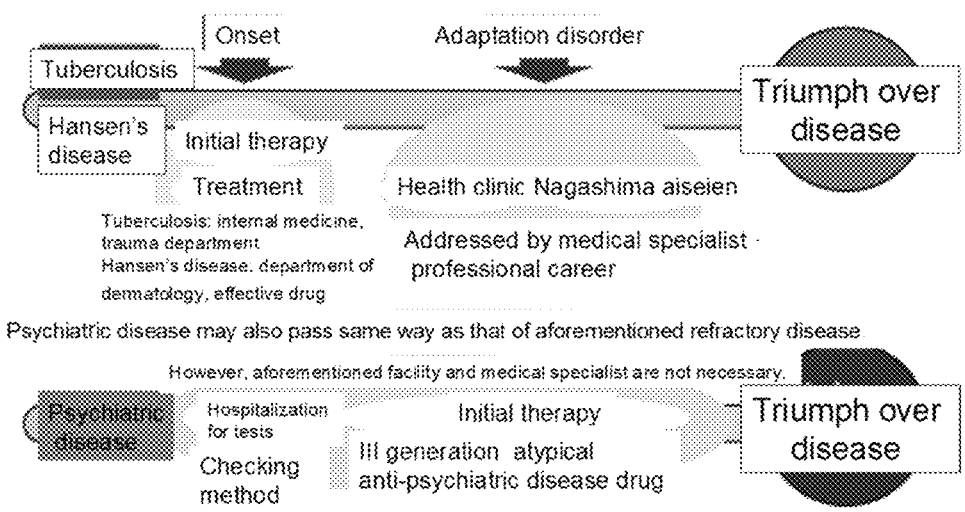
FIG. 4 shows an example of disease therapy.
Figure 5:
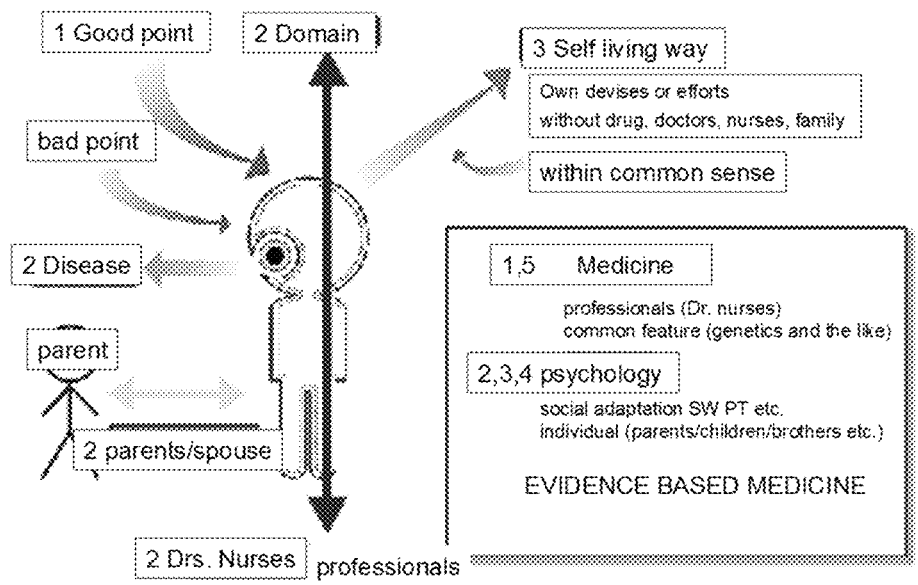
FIG. 5 is an illustration of evidence-based medicine.
Figure 6:
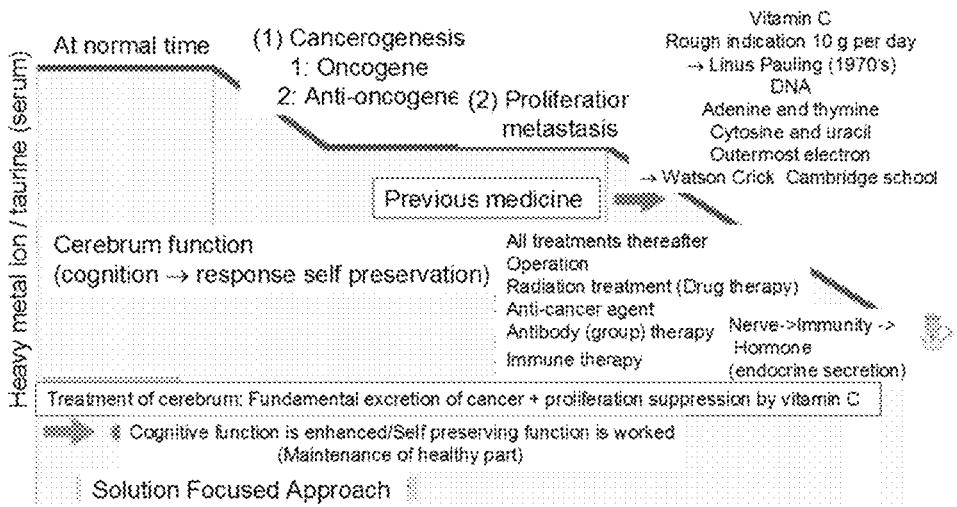
FIG. 6 is an illustration of the Solution Focused Approach.

The present invention will be explained below. It is to be understood that expression of a single form also includes a concept of its plural form throughout the present specification, unless otherwise indicated. Therefore, it is to be understood that an article or an adverb in a single form (e.g. "a", "an", "the" and the like) includes a concept of its plural for unless otherwise indicated. In addition, it is to be understood that a word used in the present specification is used in a sense normally used in the art, unless otherwise indicated. Therefore, unless otherwise defined, all the specialized terminology and scientific and technical words used the present specification have the same meanings as those that are generally understood by a skilled person in the art to which the present invention pertains. When conflicted, the present specification (including definition) shall control.

(Definition)

The following is a list of definition of terms particularly used in the present specification.

The "disease" which is a subject of the present invention may be any disease, and it can usually be a disease or a disorder which is associated with a disorder directly or indirectly associated with the immune state or homeostasis of a body. Examples of such a disease are not limited to, but include cancer, an infectious disease with viruses or bacterium, allergy, hypertension, hyperlipemia, diabetes, cardiac disease, brain infarction, dementia, obesity, arteriosclerotic disease, infertility, neuropsychiatric disease, cataract, progeria, and ultraviolet radiation hypersensitivity.

The "disorder" which is a subject of the present invention can be an arbitrary disorder associated with abnormality of a body.

In one embodiment, the disease or disorder can be a circulatory (blood cell or the like) disease or disorder. Examples of such a disease or disorder are not limited to, but include anemia (e.g. anaplastic anemia (particularly serious anaplastic anemia), renal anemia, cancerous anemia, secondly anemia, or refractory anemia), cancer or tumor (e.g. leukemia) and hematopoietic failure after chemotherapy treatment thereof, thrombocytopenia, acute myelocytic leukemia, (particularly, first remission period (High-risk group) second remission period or remission periods thereafter) acute lymphatic leukemia (particularly, first remission period, second remission period or remission periods thereafter), chronic myelocytic leukemia (particularly, chronic period, transition period), malignant lymphoma (particularly, first remission period (High-risk group), second remission period or remission periods thereafter), and multiple myeloma (particularly, early stage after sideration).

In another embodiment, the disease or disorder may be a nervous disease or disorder. Examples of such a disease or disorder are not limited to, but include dementia, stroke and sequela thereof, brain tumor, and spinal damage.

In another embodiment, the disease or disorder may be an immune disease or disorder. Examples of such a disease or disorder are not limited to, but include the following: T cell deficiency, and leukemia.

In another embodiment, examples of the disease or disorder may be a motor or skeletal disease or disorder. Examples of such a disease or disorder are not limited to, but include: bone fracture, osteoporosis arthral bone dislocation, subluxation, ligament rupture, ligament damage, osteoarthritis, bone sarcoma, Ewing's sarcoma, osteogenesis imperfecta, and osteochondrodysplasia.

In another embodiment, the disease or disorder may be a dermal disease or disorder. Examples of such a disease or disorder are not limited to, but include the following: atrichia melanoma, skin malignant lymphoma, angiosarcoma, histiocytosis, bullosis, pustulosis, dermatitis, and eczema.

In another embodiment, the disease or disorder may be an endocrine system disease or disorder. Examples of such a disease or disorder are not limited to, but include hypothalamus•pituitary gland disease, thyroid gland disease, accessory thyroid gland (parathyroid gland) disease, renal cortex•medullae disease, saccharidoses, abnormal lipid metabolism, abnormal protein metabolism, abnormal nucleic acid metabolism, congenital abnormal metabolism (phenyl ketonuria, galactosemia, homocystinuria, maple syrup urine disease), analbuminemia, ascorbic acid synthesizing ability deficiency, hyperbilirubinemia, hyperbilirubinuria, kallikrein deficiency, mast cell deficiency, diabetes insipidus, vasopressin secretion abnormality, dwarfism, Wolman's disease (acid lipase deficiency), and mucopolysaccharidosis type VI.

In another embodiment, the disease or disorder can be a respiratory disease or disorder. Examples of such a disease or disorder are not limited to, but include the following: lung disease pneumonia or lung cancer), and bronchial disease.

In another embodiment, the disease or disorder can be an alimentary system disease or disorder. Examples of such a disease or disorder are not limited to, but include the following: esophagus disease (e.g. esophagus cancer), stomach•duodenum disease (e.g. stomach cancer or duodenum cancer), small intestine•large intestine disease (e.g. large intestine polyp, colon cancer or rectum cancer), biliary tract disease, liver disease (e.g. cirrhosis hepatic, hepatitis (type A, type B, type C, type D, type E or the like), fulminant hepatitis, chronic hepatitis, primary liver cancer, alcoholic liver disorder or drug liver disorder), pancreatic disease (acute pancreatitis, chronic pancreatitis, pancreas cancer, cystic pancreas disease), peritonea•abdominal wall•diaphragma disease (hernia or the like), and Hirschsprung's disease.

In another embodiment, the disease or disorder can be a urinary disease or disorder. Examples of such a disease or disorder are not limited to, but include the following: kidney disease (renal failure, primary glomus disease, renal vascular disorder, convoluted tubule functional abnormality, interstitial renal disease, renal disorder due to systemic disease or kidney cancer), and bladder disease (inflammation of the bladder or bladder cancer).

In another embodiment, the disease or disorder can be a reproductive system disease or disorder. Examples of such a disease or disorder are not limited to, but include the following: male reproductive disease (male infertility, prostate hypertrophy, prostate cancer or testis cancer), and female reproductive disease (female infertility, ovary functional disorder, fibroid, adenomyosis of the uterus, uterus cancer, endometriosis, ovary cancer or villosity disease).

In another embodiment, the disease or disorder can be a circulatory disease or disorder. Examples of such a disease or disorder are not limited to, but include the following: heart failure, angina cordis, myocardial infarction, arrhythmia, valvular disease, cardiac muscle•capsula cordis disease, congenital cardiac disease (e.g. defect of the interatrial septum, interventricular septal defect, patent ductus arteriosus or tetralogy of Fallot), arterial disease (e.g. arteriosclerosis or aneurism), venous disease (e.g. varicosity), and lymph duct disease (e.g. lymphatic edema).

Examples of the disease or disorder curable by an immune system which can be treated or ameliorated by the present invention are not limited to, but include atopic dermatitis, and chronic arthritis rheumatoid.

Examples of the cancer which can be treated or ameliorated by the present invention are not limited to, but include brain tumor, leukemia, stomach cancer, lung cancer, liver cell cancer, metastatic cancer, primary breast cancer, recurrent breast cancer, primary liver cancer, biliary tract cancer, pancreas cancer, kidney cancer, prostate cancer, testis cancer, uterine corpus cancer, ovary cancer, lung small cell cancer, leukemia, biliary tract cancer, digestive system cancer, large intestine cancer, liver cancer, metastatic liver cancer, cervix uterine cancer, colon cancer, rectum cancer, thyroid cancer, breast cancer, urinary cancer, uterus cancer, esophagus cancer, cystic mole, chorionic cancer, ectopic HCG producing tumor, cholecystis cancer, bile duct cancer, neuroblastoma, maxillary cancer, oral cavity cancer, oral cavity bottom cancer, genitourinary cancer, thyroid cancer, malignant lymph (Hodgkin and non-Hodgkin), bladder cancer, hematopoietic tumor, prostate cancer accompanying bone metastasis, last stage cancer, neuroblast tumor, lung small cell cancer, lung non-small cell cancer, melanocytoma, gastrinoma, insulinoma, carcinoid, malignant tumor accompanying hypercalcemia, adult T cell leukemia, vulva cancer, skin cancer, upper airway cancer, head and neck cancer, teratoma, bladder cancer, β cell leukemia, testis tumor, digestive system cancer, acute myelocytic leukemia, acute lymphatic leukemia, malignant tumor, primary liver cancer, sarcoma, malignant melanoma, lymphoma, and lung squamous epithelium cancer.

Examples of the infectious disease which can be treated or ameliorated by the present invention are not limited to, but include HBV infectious disease, HCV infectious disease, various bacterial infectious diseases, fungal infectious disease, viral infectious disease, HIV-1 infection, HIV-2 infection, herpesvirus (including HSV-1, HSV-2, CMV, VZV, HHV-6, HHV-7, and EBV without limitation) infection, adenovirus infection, poxvirus infection, human papilloma virus infection, hepatitis virus (e.g. including HAV, HBV, and HCV without limitation) infection, *Helicobacter pylori* infection, parasitic organism infection, and HTLV-1 infection.

Examples of the lifestyle disease which can be treated or ameliorated by the present invention are not limited to, but include diabetes, arteriosclerosis (including brain infarction, angina cordis, and myocardiac infarction without limitation), hypertension, malignant tumor, emphysema, and regressive change of bone.

Examples of the parasite disease which can be treated or ameliorated by the present invention are not limited to, but include amebiasis, babesiasis, coccidiosis, cryptospolidiosis, dientamebiasis, dourine, external parasitic organism infectious disease, giardiasis, helminthiasis, leishmaniasis, *Schistosoma* infection, theileriasis, toxoplasmosis, trypanosomiasis, as well as *Trichomonas* infection and sporozoan (e.g. *Plasmodium virax, Plasmodium falciparium, Plasmodium malariae*, and *Plasmodium ovale*) infection, scabies, Japanese river fever, eye infection, intestine disease bloody flux, giardiasis) liver disease, lung disease, opportunistic infection disease (e.g. AIDS-associate), and malaria.

Examples of the immune exacerbation which can be treated or ameliorated by the present invention are not limited to, but include allergic dermatitis and psoriasis.

Examples of the immunodeficiency which can be treated or ameliorated by the present invention are not limited to, but include pyoderma, oral candidiasis, and virus infectious disease.

Examples of the drug poisoning which can be treated or ameliorated by the present invention are not limited to, but include alcoholic poisoning, nicotine poisoning, and heroin poisoning.

The "lifestyle disease" in the present specification refers to an arbitrary disease in which cause of a disease is gradually spread through repetition of a way of daily life or bad habit, and symptom comes out when the relevant person reaches a certain age. Examples thereof include diabetes, hypertension, hyperlipemia, gout (hyperuricemia), obesity, arteriosclerosis, brain infarction, myocardiac infarction, pancreatitis, respiratory disease, stomach•duodenum ulcer, hepatic function disorder, osteoporosis, cancer, and periodontal disease, and the lifestyle disease is a category according to a disease classifying method which puts a weight on cause as compared with the aforementioned sideration site. Since it is thought that in such a lifestyle disease, symptom is exacerbated due to reduction in the cognitive ability of a brain in case, is understood that the method of the present invention can act on any of these diseases.

According to the present invention, in treatment of the aforementioned diseases, any negative effect due to the previous drug therapy was avoided. Enablement of curing of last stage cancer which was not previously cured certainly can be said to be the remarkable effect which was impossible or difficult in conventional techniques.

In one embodiment, the present invention can be useful in formulating an agent for preventing, ameliorating or treating central disease (e.g. apoplexia cerebri, apoplexia cerebri sequelae, delayed nerve cell death, Alzheimer's disease, dementia, eating disorder, Parkinson's disease, multiple sclerosis, or Creutzfeldt-Jakob disease), inflammatory disease (e.g. allergy, asthma or rheumatoid), circulatory disease (e.g. ischemic disorder, reperfusion disorder, hypertension, heart hypertrophy, angina cordis or arteriosclerosis), cancer (e.g. non-small cell lung cancer, ovary cancer, prostate cancer, stomach cancer, bladder cancer, breast cancer, cervix uteri cancer, colon cancer or rectum cancer), metabolism disease (e.g. diabetes, diabetic complication, obesity, arteriosclerosis, gout, cataract, hepatitis, amyloidosis or Wilson's disease), immune disease (e.g. autoimmune disease), digestive organ disease (e.g. stress ulcer, acute pancreatitis, inflammatory bowel disease, ulcerous colitis, stomach ulcer, duodenum ulcer, gastric inflammation or reflux esophagitis), autoimmune disease (chronic arthritis rheumatoid, multiple sclerosis or systemic erythematodes), degenerative disease (amyloidosis, hemosiderosis or Wilson's disease), ischemic nerve cell damage (apoplexia cerebri, apoplexia cerebri sequelae or delayed nerve cell death), ischemic•reperfusion damage, cystic fibrosis, malignant tumor, infectious disease (multi organ failure due to sepsis or acute respiratory distress syndrome), liver failure, kidney failure, drug poisoning, heavy metal poisoning, radiation damage, ultraviolet damage (damage of skin, or lens or retina of eye due to ultraviolet-ray), other living body invasion (damage of skin or tissue due to heat or acid), viral disease (type B hepatitis, type C hepatitis, type D hepatitis, type E hepatitis, acquired immunodeficiency syndrome or adult leukemia) or aging.

In the present specification, it has been known that, at least actually, type B hepatitis, type C hepatitis, acquired immunodeficiency syndrome (AIDS), diabetes, diabetic complication, prostate hypertrophy, gout, hepatitis, autoimmune disease, malignant lymphoma, pancreas cancer, cervix uteri cancer, oral cavity bottom cancer, kidney cancer, hypertension, ulcerous colitis, chronic arthritis rheumatoid, chronic granulomatosis, inflammatory bowel disease, neutropenia and neutrophilia, as well as other disease, for example, substantially arbitrary cancer, viral disease, metabolism disease, circulatory disease, digestive organ disease, inflammatory disease, central disease, immune disease, infectious disease and lifestyle disease seem to be cured.

In the present invention, by increasing the disease cognitive ability of a brain, it was revealed that an arbitrary disease can be cured. In principle, since a brain can cognize any disease, it is to be understood that the present invention is effective for an arbitrary disease.

In the present specification, "intravital" or "in vivo" refers to the inside of a living body. In a particular context, "intravital" refers to a position at which an objective tissue or organ is to be disposed.

In the present specification, "subject" refers to an organism to which treatment of the present invention is applied, and is also called "patient". The patient or the subject can be preferably a human.

In another embodiment, in the present invention, it is planned that a drug (e.g. anticancer age is used together. Such a drug can be an arbitrary drug known in the art and, for example, such a drug can be an arbitrary drug (e.g. anti-cancer agent or antibiotic) known in pharmacy. Naturally, such a drug can be two or more kinds of other drugs. Preferably, the drug can be administered at the same time with or at a different time from thermotherapy. Examples of such a drug include drugs listed in Japanese Pharmacopoeia latest edition, US Pharmacopoeia latest edition, or latest edition of Pharmacopoeia in other countries.

In the present specification, the "major tranquilizer" is one of psycholeptics (generic name of a drug which suppressively acts on psychiatric function or emotion, and gives little change to other central nervous function) and, among them, refers to a drug by which anxiety or tension is relieved, and conscious disorder or sleeping does not occur at a normal dose. (On the other hand, a minor tranquilizer is used for the purpose of treating sleeping induction or anti-epilepsia, in addition to treating anxiety, agrypnia, or nervous disease with a drug). This also called neuroplegica or antipsychotic drug. Reserpine (component of Indian snakeroot), chlorpromazine, haloperidol, and lithium carbonate belong to this. Examples of the major tranquilizer which is representatively used include a butyrophenone derivative (e.g. haloperidol, spiperone or timiperone) phenothiazine derivative (fluphenazine maleate, trifluoperazine maleate, perphenazine, or prochlorperazine), a benzamide derivative (nemonapride or the like) an atypical antipsychotic drug (risperidone or the like) and the like.

In the present specification, an "amount" or a "dose" for the "psychiatric disease treatment" can be set based on Pharmacopoeia or a minimum amount which is normally used. For haloperidol, at an initial stage, an amount is started with 0.75 to 2.25 mg a day and gradually increased, and since a maintenance amount is 6 mg a day, and a maximum amount per day is 40 mg, 0.75 mg is adopted as a standard amount. For spiperone, in the first week, an amount is started with 0.45 to 1.5 mg, and since 1.5 to 4.5 mg a day is used thereafter, 0.45 mg is adopted as a standard amount. For timiperone, at an initial stage, an amount is started with 0.5 to 3 mg a day, and since an amount is gradually increased to 3 to 12 mg a day thereafter, 0.5 mg is adopted as a standard amount.

In the present specification, the "vitamin C" (ascorbic acid, cevitamic acid, hexuronic acid) is a colorless crystalline substance ($C_6H_8O_6$, molecular weight 176.13), a melting point is 190 to 192° C., and an L body of ascorbic acid is vitamin C. Specific rotation degree=+23° (c=1, in water). It is soluble in water and insoluble in ethanol. It is a substance which is weak to heat, and has a strong reducing force and an ultraviolet absorption maximum of 265 nm (aqueous solution). It has an oxidation reduction potential of +0.058 V (pH 7.0). Its natural body it contained in fresh fruit juice, green tea, radish, or green leaf at a large amount, and has the anti-scorbutic activity. A D body does not have that efficacy. It exhibits acidity in an aqueous solution because one of enol-form hydroxy groups is dissociated, and it makes a water-soluble neutral monoalkali salt. It is thought that it is involved in an oxidation reduction system, and exhibits the activity as a vitamin in a living body. It is present in adrenal gland at a particularly large amount in an animal body, and is contained also in the liver, pituitary gland, corpus luteum, and thymus at a large amount. It easily undergoes reversible oxidation by various oxidizing agents, free oxygen (in the presence of copper) or polyphenol oxidizing enzyme, specifically, ascorbic acid oxidizing enzyme, and converted into dehydroascorbic acid, thereby, they become an electron donor and an electron receptor, respectively. Thus, it is presumed that it plays a role of biological oxidation reduction as a hydrogen transporter. Ascorbic acid functions in hydroxylation of proline and lysine in collagen biosynthesis, metabolism of tyrosine and biosynthesis of catecholamine, detoxication of a living body foreign matter, suppression of production of nitrosoamine, hydroxylation of cholesterol into 7α-cholesterol, absorption of iron, reduction of cytochrome c, activation of NADH reductase, metabolism of copper, and immune activation. Ascorbic acid deficiency (vitamin deficiency) is mainly involved in deficiency of collagen biosynthesis, and is characterized in bleeding tendency such as scorbutus. It appears in a human, a monkey and a guinea pig lacking α-gulono-γ-lactone oxidase for ascorbic acid synthesis, but a necessary amount is sufficiently synthesized in a body of a rat, a dog and a rabbit. In its synthesis route, L-gulono-δ-lactone is produced from D-glucose via L-glucuronic acid and L-gulonic acid and, further, L-gulono-γ-lactone oxidase acts thereon to produce ascorbic acid. Primate including a human, an elephant, a guinea pig, a certain bird, a bat, and fish is genetically deficient in L-guluno-γ-lactone oxidase which catalyzes a final stage, and can not bio-synthesize ascorbic acid. Ascorbic acid is required at a largest amount among vitamins, a necessary amount a day for an adult is about 50 mg, and a minimum necessary amount is 6.5 mg. For quantitation, a method of utilizing reduction of an indophenol dye, 2,4-dichlorophenol indophenol is most frequently used. In the present invention, it is preferable to administer an artifact of vitamin C.

In the present invention, the "drip infusion" refers to drip infusion of a physiological buffer with or without specified components. As used in the present specification, any substance may be used as the drip infusion as far as it is a physiological buffer which prevents elevation of a body temperature. Representative examples include a physiological buffer containing maltose.

In the present specification, the "physiological buffer" refers to an arbitrary buffer which can be physiologically adapted. Examples of such a physiological buffer include a physiological saline (sodium chloride solution prepared so as to be isotonic with a body fluid component (particularly, serum), normally 0.9% NaCl: also called normal saline (a name of US Pharmacopoeia regarding a sodium chloride sterile aqueous is solution isotonic with a body fluid)), a physiological salt solution (a mixed solution of salts used as a medium solution which makes isolated organs or tissues retain the normal function over a long term; a cation component of a solution is mainly Na+, and $K^+$, $Ca^{2+}$ and $Mg^{2+}$ are added thereto and, further, a buffer such as sodium bicarbonate $NaHCO_3$ and sodium dihydrogen phosphate $NaH_2PO_4$ are added to adjust a pH; glucose as an energy source is added in some cases), a Japanese Pharmacopoeia physiological saline, a Japanese Pharmacopoeia glucose injection solution, a 10% maltose injection solution, a Ringer's solution, a Lock's solution and a Tyrode's solution. Specifically, an Aldofed injection solution can be adopted.

In the present specification, the "antidepressant drug" or the "antidepressive drug" refers to a medicament which relieves oppression by enhancing the central activity of sympathetic nerve. Examples thereof include imipramine and tranylcypromine. In the present specification, when blood potassium is decreased, it is administered. Specifically, it is preferable that fluvoxamine maleate is administered.

In the present specification, the "iron agent" is a drug containing iron as an ingredient, and serves for the purpose of increasing blood. Examples thereof include iron lactate, an on iodide syrup, iron citrate, and iron sulfate. Preferably, sodium ferrous citrate is used, being not limiting.

(Administration•Infusion•Medicament)

A medicament prepared with the factor of the present invention can be provided in an arbitrary preparation form as far as it is a form suitable for introduction into an organism. Examples of such a preparation form include solutions, injectables, and sustained release agents. Examples of an administration method include oral administration, parenteral administration (e.g. intravenous administration, intramuscular administration, subcutaneous administration, intradermal administration, mucosal administration, rectal administration, vaginal administration, local administration to an affected part, or dermal administration), and direct administration to an affected part. A form of delivery to a brain is preferable. Formulations for such administration can be provided in an arbitrary preparation form. Examples of such a preparation form include solutions, injectables, and sustained release agents. The composition and the medicament of the present invention, when administered systemically, can be a form of an aqueous solution which does not contain pyrogen, and can be received orally. Preparation of such a pharmaceutically acceptable protein solution is within the technical range of a person skilled in the art, provided that considerable attention is paid to pH, isotonicity and safety.

Injectables can be prepared by the method which is well-known in the art. For example, after being dissolved in a suitable solvent (physiological saline, buffer such as PBS or sterilized water), injectables can be prepared by filtration sterilization with a filter and, then filling in a sterilized container (e.g. ampoule or the like). The injectables may contain a conventional pharmaceutical carrier if necessary. A non-invasive administration method using a catheter can also be used.

In one embodiment, the medicament of the present invention can be provided in a sustained release form. A dosage form in the sustained release form can be any form known in the art as far as it can be used in the present invention. Such a form can be, for example, a rod-like (pellet-like, cylinder-like, or needle-like) form, a tablet form, a disk-like form, a spherical form, or a sheet-like form. A method of preparing the sustained-release form is known in the art, and is described, for example, in Japanese Pharmacopoeia, US Pharmacopoeia, and Pharmacopoeia in other countries, and examples of the method of preparing the sustained-release agent (sustaining administration agent) include a method utilizing dissociation of a drug from a complex, a method of preparing an aqueous suspension injection solution, a method of preparing an oily injection solution or an oily suspension injection solution, and a method of preparing an emulsion injection solution (o/w-type or w/o-type emulsion injection solution).

The composition or the kit of the present invention can also contain a material compatible with a living body. This material compatible with a living body can contain at least one member selected from the group consisting of silicone, collagen, gelatin, a copolymer of glycolic acid and lactic acid, an ethylene-vinyl acetate copolymer, polyurethane, polyethylene, polytetrafluoroethylene, polypropylene, polyacrylate and polymethacrylate. Silicone is preferable because of easy molding. Examples of the biodegradable polymer include collagen, gelatin, a polymer or a copolymer synthesized by catalyst-free dehydration polycondensation from one or more kinds of members selected from the group consisting of α-hydroxycarboxylic acids (e.g. glycolic acid, lactic acid, and hydroxybutyric acid), hydroxydicarboxylic acids (e.g. malic acid) and hydroxytricarboxylic acids (e.g. citric acid), or a mixture thereof, poly-α-cyanoacrylic acid ester, polyamino acid (e.g. poly-γ-benzyl-L-glutamic acid), and polyacid anhydride such as a maleic anhydride-based copolymer (e.g. styrene-maleic acid copolymer). A form of polymerization may be any of random, block and graft and, when α-hydroxycarboxylic acids, hydroxydicarboxylic acids, or hydroxytricarboxylic acids have an optically-active centre in a molecule, any of a D-body, an L-body, and a DL-body can be used. Preferably, a copolymer of glycolic acid lactic acid can be used.

In the present specification, the "instruction" describes explanation of a method of administering the medicament of the present invention to a person who performs administration such as a physician, or a patient. This instruction describes statement of instructing administration of the medicament of the present invention. In addition, statement of instructing administration (e.g. via injection) to a skeletal muscle as an administration site may be described in the instruction. This instruction is produced according to a format prescribed by a regulatory agency (e.g. Ministry of Health, Labor and Welfare in Japan, or Food and Drug Administration (FDA) in USA) in a country where the present invention is implemented, and there is described to the effect that the instruction was approved by the regulatory agency. The instruction is a so-called package insert and is usually provided by a paper medium, being not limiting. For example, the instruction can be provided by a form of an electronic medium (e.g. homepage provided on the Internet or electronic mail).

The frequency at which the composition of the present invention is given a subject can be easily determined by a person skilled in the art, in view of the use object, and the age, size, sex, medical history, and a treatment process of a subject. Examples of the frequency include administration once to several times a day, and daily to once per several months (e.g. once a week to once a month). It is preferable that administration once a week to once a month is performed while following-up the course.

An amount of the composition, the compound or the medicament used in the method of the present invention can be easily determined by a person skilled in the art, in view of the use object, and the age, size, sex and medical history of a subject, a form or a kind of a polypeptide, a nucleic acid, a composition, a medicament, and a form or a kind of a cell.

In the present specification, the "subject" refers to an organism to which treatment of the present invention is applied, and also to a "patient". The patient or the subject can be preferably a human.

A solvent used for formulation of a medicament in the present invention can have either of an aqueous or non-aqueous nature. Further, its vehicle can contain other formulation materials for altering or maintaining a pH, osmolarity, viscosity, cleanness, color, sterilizing property, stability, isotonicity, disintegrating rate, or odor. Similarly, the composition of the present invention can contain other formulation materials for altering or maintaining a release rate of an active ingredient, or promoting absorption or permeation of an active ingredient.

The present invention, when formulated as a medicament or a pharmaceutical composition, can be prepared for storage in a form of a lyophilized cake or an aqueous solution, by mixing, if necessary, a physiologically acceptable carrier, an excipient or a stabilizer ((Remington's Pharmaceutical Sciences, 18th Edition, A. R. Gennaro, ed., Mack Publishing Company, 1990), and a selected composition having a purity to a desired degree.

Examples of such a pharmaceutically acceptable factor are not limited to, but include: an antioxidant, a preservative, a coloring material, a flavor material, a diluent, an emulsifier, a suspending agent, a solvent, a filler, a bulking agent, a buffer, a delivery vehicle, a diluent, an excipient and/or an agricultural or pharmaceutical adjuvant. Representatively, in the medicament of the present invention, an active ingredient (e.g. polypeptide or nucleic acid) of the present invention can be administered in a form of a composition together with one or more physiologically acceptable carriers, excipients, or diluents. For example, the suitable vehicle can be water for injection, a physiological solution, or an artificial brain spinal liquid, and other substances which are general to a composition for parenteral administration can be supplemented to them. Such acceptable carriers, excipients or stabilizers are non-toxic to a recipient, and preferably inert at an administration amount and a concentration used, and examples thereof include the following: phosphate, citrate, other organic acids; antioxidant (e.g. ascorbic acid); low molecular weight polypeptide; protein (e.g. serum albumin, gelatin, or immunoglobulin); hydrophilic polymer (e.g. polyvinylpyrrolidone); amino acid (e.g. glycine, glutamine, asparagine, arginine or lysine); monosaccharide, disaccharide and other carbohydrates (including glucose, mannose, maltose or dextrin); chelating agent (e.g. EDTA); sugar alcohol (e.g. mannitol or sorbitol); salt forming counterion (e.g. sodium); and/or nonionic surface active agent (e.g. Tween, pluronic or polyethylene glycol (PEG)).

The injectable can be prepared by a method well-known in the art. For example, the injectable can be prepared by dissolving an ingredient in a suitable solvent (physiological saline, buffer such as PBS, or sterilized water), filtration-sterilizing this with a filter and, then, filling this into a sterile container (e.g. ampoule). This injectable may contain a conventional pharmaceutical carrier, if necessary. An administration method using a non-invasive catheter can also be used. Examples of the suitable carrier include a neutral buffered physiological saline, and a physiological saline mixed with serum albumin. Preferably, the medicament of the present invention can be formulated as a lyophilized agent using a suitable excipient (e.g. sucrose). Other standard carriers, diluents and excipients can be contained, if necessary. Other illustrated composition contains a Iris buffer at a pH of 7.0 to 8.5, or an acetate buffer at a pH of 4.0 to 5.5, and these can further contain sorbitol or a suitable substitute therefor. A pH of the solution should be selected based on the relative solubility of an active ingredient of the present invention, at various pHs.

A procedure of formulating the preparation of the present invention is known in the art, and is described, for example, in Japanese Pharmacopoeia, US Pharmacopoeia, or Pharmacopoeia in other countries. Therefore, as far as there is the description of the present specification, a person skilled in the art can determine an amount or frequency of a medicament to be administered, without undue experiment.

In another embodiment, in the present invention, it is planned to further administer other drugs. Such a drug can be an arbitrary drug known in the art and, for example, such a drug can be an arbitrary drug known in pharmacy (e.g. antibiotic). Naturally, such a drug can be two or more kinds of other drugs. Examples of such a drug include drugs listed, for example, in Japanese Pharmacopoeia latest edition, US Pharmacopoeia latest edition or latest edition of Pharmacopoeia in other countries.

A disease which is a subject of the present invention is cancer. In the present specification, she "cancer" refers to a general malignant tumor.

In the present specification, the "solid cancer" refers to cancer having a solid shape, and is a concept contrary to hematopoietic tumor such as leukemia. Examples of such solid cancer are not limited to, but include breast cancer, liver cancer, stomach cancer, lung cancer, head and neck cancer, cervix uteri cancer, prostate cancer, retinoblastoma, malignant lymphoma, esophagus cancer, brain tumor, and bone tumor.

(Preferable Embodiments)

A preferable embodiment of the present invention will be explained below. An embodiment provided below is provided for better understanding of the present invention, and it is understood that the scope of the present invention is not limited by the following description. Therefore, it is apparent that a person skilled in the art can appropriately conduct alteration within a range of the present invention in view of the description of the present specification.

Although it is arbitrary, a basis of treatment of the present invention can be performed roughly at two stages. (1) If necessary, a body is cooled by drip infusion and, if necessary, two kinds antibiotics are given. (2) If necessary, by cooling a brain by drip infusion, safety of a healthy part, which is 97% of a brain, can be maintained. Since a brain is altered in nature at 38.5° C. or higher, this is prevented to certainly leave a healthy. If a brain can be cooled, a procedure other than drip infusion can be used. In addition, 60 to 80 thousand brain cells are dying a day. In addition, there can be bacterial infection in a urinary tract or lung of a patient. Then, in order to clean these dead cells, if necessary, the function of macrophage (phagocytizing cell), leukocyte or lymphocyte can be also enhanced using an antibiotic. Macrophage and the like take a bacterium and a foreign matter into a cell, digest them, and are greatly involved in restoration of inflammation or immune action. (2) Parallel with this, a combination of vitamin C and a major tranquilizer (strong tranquilizer) of the present invention is ingested. Vitamin C is ingested usually at 3 grams (capacity: 600 mg) in a tablet, or normally at 9 grams (capacity: 1800 mg) which is well enough. Vitamin C used in treatment in a preferable embodiment is slightly different from natural vitamin C in a structure, because this is far more effective. In addition, there is no problem that if vitamin C is ingested with any drug or food. This has been found out by a long-term clinical experience. In the present invention, it was discovered that, by this combination, an ability of cognizing which part of one's body is ill can be enhanced by a brain. It has been found out that, by maintaining a healthy part early, and enhancing the cognitive ability of a brain like this, almost all diseases (e.g. cancer and psychiatric disease) are directed to restoration. Also in senile dementia, an effective therapy due to evidence-based medicine was attained by ingesting a combination of drip infusion and an antibiotic, if necessary, which is a basis of therapy cure by early therapy, as well as a combination of vitamin C and a major tranquilizer of the present invention.

In one aspect, the present invention provides a medicament for treating or preventing a disease, including a combination of a major tranquilizer, and vitamin C or a salt thereof.

In another aspect, the present invention provides a method for treating or preventing a disease, including a step of administering a major tranquilizer, and vitamin C or a salt thereof to a subject suffering from the disease.

In one embodiment, the major tranquilizer used in the medicament of the present invention can be a butyrophenone derivative, a phenothiazine derivative, or a benzamide derivative.

In another embodiment, the butyrophenone derivative used in the present invention as a major tranquilizer can be haloperidol, spiperone or timiperone, preferably haloperidol.

In one embodiment, the major tranquilizer to be administered is preferably administered at an amount which is half dose of an amount of psychiatric disease treatment, being not limiting.

In another embodiment, a dose of a major tranquilizer administered in the present invention can be a daily dose of 0.25 mg to 1 mg in terms of haloperidol. It has been found out in the present invention that, by using a dose smaller than an amount used in a psychiatric disease, the cognitive ability of a brain can be enhanced.

Preferably, the major tranquilizer is administered before bedtime, being not limiting.

Vitamin C used in the present invention can be ascorbic acid which is an artifact. This is because it has been empirically found out that the artifact is a several-fold to a several thousands-fold better in the effect than vitamin C which is a natural substance.

In one embodiment of the present invention, in the medicament of the present invention, vitamin C is contained so that a daily dose of 600 mg to 1800 mg as an effective amount is administered, being not limiting.

In one embodiment, vitamin C may be further combined with pantothenic acid or a salt thereof, and this is not necessarily essential.

In the combinatorial therapy of the present invention, it is preferable to further combine drip infusion. Without desiring to be bound by a theory, it was found out in the present invention that it is optimal for cognizing a disease of a brain to maintain a body, particularly a brain, at a low temperature. Therefore, it is to be understood that, as a solution used in drip infusion, any solution may be used as far as a body, particularly, a brain can be maintained at a low temperature. In a preferable embodiment, a physiological buffer supplying energy is preferable. For supplying energy, glucose or maltose can be utilized. Maltose is preferable. This is because maltose can supply energy which is about 2-fold energy of glucose at the same osmotic pressure. It is to be understood that, as the physiological buffer, any buffer can be used as far as it is physiologically compatible. Examples of the physiological buffer containing maltose include an Aldofed injection solution. In an embodiment, this drip infusion is administered until appetite is worked up.

In another embodiment, the medicament of the present invention can be characterized in that an antidepressant is combined. The antidepressant can be administered when blood potassium is decreased. Examples of such an antidepressant include fluvoxamine maleate. The antidepressant to be administered in the present invention is preferably administered daily, or may be administered arbitrarily.

In another embodiment, the medicament of the present invention can be characterized in that an iron agent is combined. In a preferable embodiment, the iron agent can include sodium ferrous citrate, but other iron agents may also be used.

In a preferable embodiment of the present invention, the combinatorial medicament of the present invention may be a combination of drip infusion and an anti-depressant, in addition to a combination of the major tranquilizer and vitamin C. In this case, the aforementioned arbitrary preferable effect is exerted.

In a preferable embodiment of the present invention combinatorial medicament of the present invention may be further combined with drip infusion and an iron agent, in addition to a combination of the major tranquilizer and vitamin C. Also in this case, the arbitrary preferable effect described above in the present specification is exerted.

In a preferable embodiment of the present invention, combinatorial medicament of the present invention may be further combined with drip infusion, an antidepressant and an iron agent, in addition to a combination of the major tranquilizer and vitamin C. Also in this case, the arbitrary preferable effect described above in the present specification is exerted.

The disease which is a subject of the present invention can be an arbitrary disease and, particularly, is remarkably characterized in that at least one disease (e.g. cancer, muscular dystrophy and Huntington's chorea) is included. The cancer which is a subject of the present invention can be large intestine cancer, colon cancer, rectum cancer, thyroid gland cancer, esophagus cancer, chorionic cancer, gallbladder cancer, neuroblastoma, maxillary cancer, oral cavity cancer, genitourinary cancer, malignant lymphoma, liver cancer, prostate cancer, lung cancer, lung cell cancer, breast cancer, stomach cancer, bladder cancer, pancreas cancer, testicle cancer, uterus cancer, uterine corpus cancer, cervix uteri cancer, ovary cancer, pharyngeal cancer, myelocystic leukemia, brain tumor, biliary tract cancer, neuroblast tumor, melanocytoma, gastrinoma, insulinoma, carcinoid, kidney cancer, testis cancer, adult T cell leukemia, vagina cancer, vulva cancer, skin cancer, upper airway cancer, head and neck cancer, teratoid, gallbladder cancer, acute myelocystic leukemia, acute lymphatic leukemia, malignant lymphoma, sarcoma, malignant melanoma, lymphoma, lung squamous epithelium cancer and spinocerebellar degeneration.

In another embodiment, a psychiatric disease such as dementia can be a subject. The remarkable effect of the present invention should be recognized in that, even at a dose which was not previously thought to be a treatment dose, a surprising curing effect can be exerted by joint use of vitamin C.

Reference literatures such as scientific literatures, patents, and patent applications cited in the present specification are incorporated by reference in their entirety in the present specification to such an extent that they are specifically described, respectively.

The present invention has been explained above by showing a preferable embodiment for easy understanding. The present invention will be explained below based on examples, but the aforementioned explanation and the following examples are provided only for the purpose of illustration, and are not provided to limit the present invention. Therefore, the scope of the present invention is not limited to the embodiments and examples which are specifically described in the present specification, and is limited only by claims.

EXAMPLES

The present invention will be explained in more detail below by way of examples, but this invention is not limited by the following examples at all. As for reagents used in the following examples, those commercially available from medicament manufacturers were used with some exceptions. A clinical trial was performed according to a standard given by the government after an informed consent was obtained from a patient as a subject.

(Cancer Marker to be Used)

In the present examples, the following cancer markers (tumor markers) were used or can be used, if necessary.

List of tumor marker normal value

| Marker name | Normal value | Main diseases as a subject |
|---|---|---|
| ACT | 21-38 mg/dl | brain tumor • leukemia • stomach cancer • lung cancer |
| AFP | 10 ng/ml or less | liver cell cancer • metastatic liver cancer |
| BCA225 | 160 U/ml or less | primary breast cancer • recurrent breast cancer |
| BFP | 75 ng/ml or less | primary liver cancer • biliary tract cancer • pancreas cancer • kidney cancer • prostate cancer • testis cancer • corpus uteri cancer • ovary cancer • lung cell cancer • leukemia |
| CA15-3 | 30 U/ml or less | primary breast cancer • recurrent breast cancer |
| CA19-9 | 37 U/ml or less | pancreas cancer • biliary tract cancer • digestive system cancer • ovary cancer • corpus uteri cancer • lung cancer |
| CA50 | 35 U/ml or less | liver cancer • biliary tract cancer • digestive system cancer • ovary cancer • corpus uteri cancer • lung cancer |
| CA72-4 | 4.0 U/ml or less | stomach cancer • large intestine cancer • ovary cancer • pancreas cancer • lung cancer • liver cancer • biliary tract cancer • breast cancer |
| CA125 | 35 U/ml or less | ovary cancer • liver cancer • biliary tract cancer • pancreas cancer |
| CA130 | 35 U/ml or less | ovary cancer • cervix uteri cancer • lung cancer • liver cell cancer • pancreas cancer • biliary tract cancer • corpus uteri cancer • stomach cancer • large intestine cancer |
| CA602 | 63 U/ml or less | same line as CA130/CA125 |
| CEA | 5.0 ng/ml or less | colon cancer • rectum cancer • pancreas cancer • biliary tract cancer • lung cancer • stomach cancer • thyroid gland cancer • breast cancer • urologic cancer • uterine cancer • liver cell cancer • esophagus cancer • ovary cancer |
| DUPAN-2 | 400 U/ml or less | pancreas cancer • biliary tract cancer • liver cell cancer • esophagus cancer • stomach cancer • large intestine cancer |
| HCG-β | 0.2 mg/ml or less | cystic mole • chorionic cancer • ectopic HCG-producing tumor |
| IAP | 500 m/ml or less | gallbladder cancer • neuroblastoma • leukemia • maxillary cancer • esophagus cancer • pancreas cancer • ovary cancer • kidney cancer • lung cancer • biliary tract cancer • oral cavity cancer • genitourinary cancer • large intestine cancer • thyroid gland cancer • malignant lymphoma • stomach cancer • bladder cancer • testis cancer • prostate cancer • cervix uteri cancer • liver cancer • breast cancer |
| ICDH | 3-10 U/l | liver cancer • metastatic liver cancer |
| KMO-1 | 5300 U/ml or less | pancreas cancer • gallbladder cancer • biliary tract cancer • liver cancer • stomach cancer • large intestine cancer • ovary cancer • (less than 8-fold) lung cancer |
| αMaro-globlin | 120-320 mg/dl | hematopoietic tumor • prostate cancer accompanying bone metastasis • last stage cancer |
| NCC-ST-439 | 7.0/ml or less | pancreas cancer • biliary tract cancer • stomach cancer • ovary cancer • corpus uteri cancer |
| NSE | 10 ng/ml or less | neuroblast tumor • lung small cell cancer • breast cancer • ovary cancer • esophagus cancer • stomach cancer • pancreas cancer • large intestine cancer • thyroid gland cancer • melanocytoma • gastrinoma • insulinoma • carcinoid |
| PAP | 30. ng/ml or less | prostate cancer |
| PIPC | 160 ng/ml or less | bone metastasis of prostate cancer |
| PIVKA-□ | less than 40 mAU/ml | cell cancer |
| PSA | 3.5 ng/ml or less | prostate cancer |
| PTHrP | 1.1 pmol/l or less | malignant tumor accompanying hypercalcemia • adult T cell leukemia |
| SCC | 1.5 ng/ml or less | cervix uteri cancer • vagina cancer • vulva cancer • skin cancer • esophagus cancer • lung cancer • upper airway cancer • head and neck cancer • teratoma • bladder cancer |
| sICAM-1 | 75 U or less | pancreas cancer • gallbladder cancer • stomach cancer • cell leukemia • ATL |
| SLX | 38 U/ml or less | lung cancer • pancreas cancer • biliary tract cancer • ovary cancer • esophagus cancer • stomach cancer • large intestine cancer • liver cancer • uterine cancer |
| r-Sm | 4.0 ng/ml or less | prostate cancer |
| SP1 | 4.0 ng/ml or less | chorionic cancer • ovary cancer • testis tumor • lung cancer • breast cancer • digestive system cancer |
| SOD | 150 ng/ml or less | ovary cancer • liver cancer • stomach cancer • leukemia |
| Span-1 | 30 U/ml or less | pancreas cancer • biliary tract cancer • liver cell cancer • stomach cancer • large intestine cancer • esophagus cancer • lung cancer • malignant lymphoma |
| STN | 45 U/ml or less | ovary cancer • stomach cancer • large intestine cancer • pancreas cancer • lung cancer |
| TK activity | 5 U/l or less | acute myelocytic leukemia • acute lymphatic leukemia • malignant lymphoma • malignant tumor |
| TPA | 70 U/l以下 | breast cancer • lung cancer • stomach cancer • large intestine cancer • primary liver cancer • biliary tract cancer • pancreas cancer • bladder cancer • prostate cancer • testis cancer • ovary cancer • cervix uteri cancer • thyroid gland cancer • sarcoma • malignant melanoma • lymphoma • leukemia |
| YH-206 | 25 U/ml or less | pancreas cancer • stomach cancer |
| Elastase 1 | 400 ng/ml or less | pancreas cancer |

-continued

| List of tumor marker normal value | | |
|---|---|---|
| Marker name | Normal value | Main diseases as a subject |
| Cytokeratin 19 fragment | 3.5 ng/ml or less | lung cancer • esophagus cancer • rectum cancer • ovary cancer • lung cancer • corpus uteri cancer thyroid gland cancer |
| Thyro-globulin | 5-30 ng/ml | thyroid gland cancer |
| CYFRA21-1 | 2.0 ng/ml以下 | lung squamous epithelium cancer • esophagus cancer • stomach cancer • large intestine cancer • ovary cancer • liver cancer • uterine cancer |

Example 1

Transverse Colon Cancer

In the present example, Mr. TM (76 year old) suffering from transverse colon cancer was treated as follows, and course of transverse colon cancer was observed. The body weight at treatment initiation was 62 kg.

(Formulation)

A Celanese (haloperidol) 0.75 mg tablet was administered before bedtime at ½ tablet a day.

6.0 g of CPG (containing mg ascorbic acid, and 18 mg of calcium pantothenate) was administered on an empty stomach.

At hospitalization, 500 ml of an Aldofed injection solution (maltose, potassium chloride, magnesium chloride, potassium hydrogen phosphate, potassium dihydrogen phosphate, sodium chloride, magnesium chloride (hexahydrate), anhydrous sodium acetate, maltose (monohydrate)) was infused at decreased appetite.

At reduction in blood potassium, SSR1 (Luvox (fluvoxamine maleate, 25 mg) two tablets) was administered.

At anemia, 1 to 2 tablets of Ferromia (sodium ferrous citrate) was administered on an empty stomach.

(Course)

When a test was performed before operation, the following test results were obtained, and the patient was diagnosed to have transverse colon cancer 15 days before the operation.
Before 4 Months from Operation
CEA 2.7 (standard value is 5.0 or less)
Ca19-9(EIA) 19 (standard value is 37 or less)
Ca50 32 (standard value is 40 or less)
Before 15 Days from Operation
CEA 16.2 (standard value is 5.0 or less)
Ca19-9(EIA) 128 (standard value is 37 or less)
Ca50 96 (standard value is 40 or less)

(Operation)

The size was 11×6 cm around ¾ of transverse colon, being Stage 4. A cancer was metastasized to mesentery lymph gland S-shape colon and the like.

Forty-two cm around transverse colon cancer was all isolated, and excised, mesentery was also excised as much as possible, and colon node jobs were anastomosed. 200 ml of stored blood was infused.

(After Operation)

The body weight at a normal time was 70 kg, while the body weight was decreased to 49 kg after operation. Cancer markers were all (−). Anemia was observed.

(Treatment)

Vitamin C, Celanese, and Luvox (25) were initiated 5 days after operation.

(Course of 3 Months Post-Operation Examination)

S-shaped colon metastasized cancer disappeared. There was no abnormality of blood, and markers were (−) Anemia was not observed.

(Prognosis)

Also after cure, equal amounts of Vitamin C, Celanese, and Luvox (25) were administered and 3 years from operation, course is good.

Example 2

Treatment of Large Intestine Cancer Patient

Next, treatment of 11 large intestine cancer patients is described.

(Treatment Method)

In principle, the same as Example 1.

(Case and Results)

The following is course of treatment of the large intestine cancer patients.

TABLE 2

| ID | Birth date | Age/Year | Disease name | Anti-cancer treatment | Dosing treatment at this time | Alive or dead |
|---|---|---|---|---|---|---|
| HS | Jan. 21, 1936 | 69 | Large intestine cancer | Lung metastasis (OP) | 21 years | Alive |
| TM | Jun. 20, 1926 | 79 | Large intestine cancer | OP | 5年 | Alive |
| MK | Mar. 21, 1945 | 60 | Large intestine cancer | 4 years after OP, dosing was stopped. Dead at 10 months at Yoga. | 4 years | Dead |
| HH | Mar. 31, 1919 | 86 | Large intestine cancer | OP | 7 years | Dead |
| SN | Apr. 30, 1914 | 91 | Large intestine cancer | | 8 Years | Dead |
| MN | Apr. 12, 1915 | 90 | Large intestine cancer | | 8 Years | Dead |
| CH | Jun. 11, 1931 | 73 | Large intestine cancer | | C only 6 years | Alive |
| TY | Dec. 11, 1952 | 52 | Large intestine cancer | OP Impossible to completely excise ( ) | 11 Years | Alive |
| KY | Sep. 22, 1939 | 65 | Large intestine cancer Uterine cancer | OP II Japanese Red Cross | 6 Years | Alive |
| MK | Jun. 21, 1919 | 86 | Large intestine cancer Transverse colon cancer | | 6 Years | Alive |

(Findings)

In all cases, patients were still alive unexpectedly, or in dead cases, the life was remarkably prolonged as compared with the previously announced life.

Example 3

Treatment of Liver Cancer Patients

Next, treatment of 7 liver cancer patients is described.
(Treatment Method)
In principle, the same as Example 1.
(Case and Results)
The following is the course of treatment of the patients.

TABLE 3

| ID | Birth date | Age/ Year | Disease name | Anti-cancer treatment | Dosing treatment at this time | Alive or dead |
|---|---|---|---|---|---|---|
| SK | Jan. 2, 1933 | 72 | Liver cancer | | 8 years | Alive |
| SK | Mar. 29, 1935 | 70 | Liver cancer | | 4 months | Alive |
| FS | Aug. 8, 1942 | 62 | Liver cancer | | | |
| TF | Jan. 6, 1933 | 72 | Liver cancer | | | |
| KM | Aug. 20, 1926 | 79 | Liver cancer | | 15 years | Alive |
| HI | Jan. 28, 1925 | 80 | Liver cancer | | 12 years | Dead |
| SH | Oct. 16, 1912 | 92 | Liver cancer | | 13 years | Dead |

(Findings)

In all cases, patients were still alive unexpectedly, or in dead cases, the life was remarkably prolonged as compared with the previously announced life.

Example 4

Treatment of Prostate Cancer Patients

Next, treatment of 6 prostate cancer patients is described.
(Treatment Method)
In principle, the same as Example 1.
(Case and Results)
The following is the course of treatment of the patients.

TABLE 4

| ID | Birth date | Age/ Year | Disease name | Anti-cancer treatment | Dosing treatment at this time | Alive or dead |
|---|---|---|---|---|---|---|
| JI | | 78 | Prostate cancer | | 3 Years | Alive |
| MK | Apr. 20, 1916 | 89 | Prostate cancer | Bladder metastasis Use of anti-cancer agent Complete disappearance | 6 Years | Dead |

TABLE 4-continued

| ID | Birth date | Age/ Year | Disease name | Anti-cancer treatment | Dosing treatment at this time | Alive or dead |
|---|---|---|---|---|---|---|
| | | | | (Japan Baptist Hospital, change of doctor Interruption Dead after 12 days) | | |
| AK | Aug. 7, 1927 | 77 | Prostate cancer | | 7 Years | Alive |
| KN | Feb. 9, 1931 | 74 | Prostate cancer | | 5 Years | Alive |
| MM | Feb. 5, 1922 | 83 | Prostate cancer | | 3 Years | Dead |
| NH | May 22, 1947 | 53 | Prostate cancer | | 5 Years | 生 |

(Findings)

In all cases, patients were still alive unexpectedly, or in dead cases, the life was remarkably prolonged as compared with the previously announced life.

Example 5

Treatment of Lung Cancer Patients

Next, treatment of 5 lung cancer patients is described.
(Treatment Method)
In principle, the same as Example 1.
(Case and Results)
Course of treatment of patients is not described due to personal reasons.
(Findings)
In all cases, patients were still alive unexpectedly, or dead cases, the life was remarkably prolonged as compared with the previously announced life.

Example 6

Treatment of Breast Cancer Patients

Next, treatment of 5 breast cancer patients is described.
(Treatment Method)
In principle, the same as Example 1.
(Case and Results)
Course of treatment of the patients is not described due to personal reasons.
(Findings)
In all cases, patients were still alive unexpectedly, or in dead cases, the life was remarkably prolonged as compared with the announced life.

Example 7

Treatment of Stomach Cancer Patients

Next, treatment of 5 stomach cancer patients is described.
(Treatment Method)
In principle, the same as Example 1.
(Case and Results)
The following is the course of treatment of a part of the patients.

TABLE 5

| ID | Birth date | Age/ Years | Disease name | Anti-cancer treatment | Dosing treatment at this time | Alive or dead |
|---|---|---|---|---|---|---|
| MM |  | 78 | Stomach cancer | OP | none | Dead |
| KH | Aug. 26, 1939 | 65 | Stomach cancer | OP | none | Alive |
| MY | Sep. 30, 1929 | 76 | Stomach cancer |  | 2 years 2 months | Alive |
| FN | Feb. 21, 1964 | 41 | Stomach cancer |  |  |  |

(Findings)
In all cases, patients were still alive unexpectedly, or in dead cases, the life was remarkably prolonged as compared with the previously announced life.

Example 8

Treatment of Bladder Cancer Patients

Next, treatment of 3 bladder cancer patients is described.
(Treatment of Method)
In principle, the same as Example 1.
(Case and Results)
The following is the course of treatment of the patients.

TABLE 6

| ID | Birth date | Age/ Year | Disease name | Anti-cancer treatment | Dosing treatment at this time | Alive or dead |
|---|---|---|---|---|---|---|
| TN | Sep. 26, 1933 | 71 | Bladder cancer |  | 15 Years | Alive |
| HH | Sep. 16, 1939 | 65 | Bladder cancer |  | 12 Years | Alive |
| HH-2 | Feb. 25, 1924 | 81 | Bladder cancer |  | none | Dead |

(Findings)
In all cases, patients were still alive unexpectedly, or in dead cases, the life was remarkably prolonged as compared with the previously announced life.

Example 9

Treatment or Pancreas Cancer Patient

Next, treatment of one pancreas cancer patient is described.
(Treatment Method)
In principle, the same as Example 1.
(Case and Results)
Course of treatment of the patient is not described due to personal reasons.
(Findings)
In this case, the life was remarkably prolonged as compared with the previously announced life, in a dead case.

Example 10

Treatment of Testis Cancer Patient

Next, treatment of one testis cancer patient is described.
(Treatment Method)
In principle, the same as Example 1.
(Case and Results)
The following is the course of treatment of the patient.

TABLE 6

| ID | Birth date | Age/ Years | Disease name | Anti-cancer treatment | Dosing treatment at this time | Alive or dead |
|---|---|---|---|---|---|---|
| KM | Sep. 24, 1961 | 43 | Testis cancer |  | 6 years 3 months | dead |

(Findings)
In this case, the life was remarkably prolonged as compared with the previously announced life, in a dead case.

Example 11

Treatment of Uterine Cancer Patients

Next, treatment of 2 uterine cancer patients is described.
(Treatment of Method)
In principle, the same as Example 1.
(Case and Results)
The following is the course of treatment of the patients.

TABLE 7

| ID | Birth date | Age/ Years | Disease name | Anti-cancer treatment | Dosing treatment at this time | Alive or dead |
|---|---|---|---|---|---|---|
| HY | May 25, 1917 | 88 | Uterine cancer |  | 15 years | Alive |
| KY | Sep. 22, 1939 | 65 | Large intestine cancer Uterine cancer | OP II Japan Red Cross | 6 years | Alive |

(Findings)
In these cases, patients are still alive unexpectedly.

Example 12

Treatment of Pharyngeal Cancer Patients

Next, treatment of 2 pharyngeal cancer patients is described.
(Treatment Method)
In principle, the same as Example 1.
(Case and Results)
Course of treatment of patients is not described due to Personal reasons.
(Findings)
In all cases, patients were still alive unexpectedly, or in dead cases, the life was remarkably prolonged as compared with the previously announced life.

Example 13

Treatment of Myelocystic Leukemia Patient

Next, treatment of one myelocystic leukemia patient is described.
(Treatment of Method)
In principle, the same as Example 1.
(Case and Results)
The following is the course of treatment of the patient.

TABLE 8

| ID | Birth date | Age/Years | Disease name | Anti-cancer treatment | Dosing treatment at this time | Alive or dead |
|---|---|---|---|---|---|---|
| SN | Apr. 20, 1910 | 95 | Bone-marrow cancer | | 16 Years | Dead |

(Findings)
In this case, the life was remarkably prolonged as compared with the announced life in a death case.

Example 14

Treatment of Ovary Cancer Patients

Next, treatment of 2 ovary cancer patients is described.
(Treatment Method)
In principle, the same as Example 1.
(Case and Results)
The following is the course of treatment of the patients.

TABLE 9

| ID | Birth date | Age/Years | Disease name | Anti-cancer treatment | Dosing treatment at this time | Alive or dead |
|---|---|---|---|---|---|---|
| FK | Dec. 13, 1943 | 61 | Ovary cancer | | 10 Years | Alive |
| AM | | 79 | Ovary cancer | | 15 Years | Alive |
| KF | Jun. 9, 1937 | 68 | Ovary cancer | | 1 year 1 month | Alive |
| TI | Sep. 4, 1931 | 74 | Ovary cancer | | 10 years | Alive |

(Findings)
In any case, the patients are still alive unexpectedly.

Example 15

Treatment of Rectum Cancer Patients

Next, treatment of 2 rectum cancer patients is described.
(Treatment Method)
In principle, the same as Example 1.
(Case and Results)
The following is course of treatment of patients.

TABLE 10

| ID | Birth date | Age/Years | Disease name | Anti-cancer treatment | Dosing treatment at this time | Alive or dead |
|---|---|---|---|---|---|---|
| IN | Nov. 24, 1928 | 76 | Rectum cancer | | 13 Years | Alive |
| SN | Apr. 19, 1922 | 83 | Rectum cancer | | 17 Years | Dead |

(Findings)
In all cases, patients were still alive unexpectedly, or in dead cases, the life was remarkably prolonged as compared with the announced life.

Example 16

Treatment of Kidney Cancer Patients

Next, treatment of 2 kidney cancer patients is described.
(Treatment Method)
In principle, the same as Example 1.
(Case and Results)
The following is course of treatment of the patients.

TABLE 11

| ID | Birth date | Age/Years | Disease name | Anti-cancer treatment | Dosing treatment at this time | Alive or dead |
|---|---|---|---|---|---|---|
| TM | Oct. 28, 1951 | 53 | Left kidney cancer | | 12 Years | Alive |

(Findings)
Also in this case, the patient is still alive unexpectedly.

Example 17

Treatment of Muscular Dystrophy Patient

Next, treatment of one muscular dystrophy cancer patient described.
(Treatment Method)
In principle, the same as Example 1.
(Case and Results)
The following is the course of treatment of the patient.

TABLE 12

| ID | Birth date | Age/Years | Disease name | Anti-cancer treatment | Dosing treatment at this time | Alive or dead |
|----|------------|-----------|--------------|-----------------------|-------------------------------|---------------|
| JM | Jul. 11, 1973 | 32 | Muscular dystrophy | Part time job is possible | 2 years 6 months | Alive |

(Findings)

Also in this case, the patient is still alive unexpectedly.

Example 18

Treatment of Huntington's Chorea Patient

Next, treatment of one Huntington's chorea patient is described.

(Treatment Method)

In principle, the same as Example 1.

(Case and Results)

The following is the course of treatment of the patient.

TABLE 13

| ID | Birth date | Age/Years | Disease name | Anti-cancer treatment | Dosing treatment at this time | Alive or dead |
|----|------------|-----------|--------------|-----------------------|-------------------------------|---------------|
| TO | Oct. 4, 1938 | 77 | Huntington's chorea | Ordinary working | 12 Years | Alive |

(Findings)

Also in this case, the patient is still alive unexpectedly.

Example 19

Treatment of Spinocerebellar Degeneration Patients

Next, treatment of 2 spinocerebellar degeneration patients is described.

(Treatment Method)

In principle, the same as Example 1.

(Case and Results)

The following is the course of treatment of the patients.

TABLE 14

| ID | Birth date | Age/Years | Disease name | Anti-cancer treatment | Dosing treatment at this time | Alive or dead |
|----|------------|-----------|--------------|-----------------------|-------------------------------|---------------|
| YS | Jan. 31, 1947 | 58 | Spinocerebellar degeneration | | 1 year 4 months | Alive |
| NH | Jun. 11, 1954 | 51 | Spinocerebellar degeneration | | 1 year 2 months | Alive |

(Findings)

In any case, the patients are still alive unexpectedly.

Example 20

Treatment of Patients with Other Diseases

Next, treatment of patients with other diseases will be described.

It is shown that this treatment is also effective in other diseases.

As described above, the present invention has been exemplified using preferable embodiments of the present invention, but it is understood that the scope of the present invention is construed only by claims. It is understood that contents of patents, patent applications and literatures cited in the present invention should be incorporated into the present specification by reference as if the contents thereof were specifically described in the specification.

INDUSTRIAL APPLICABILITY

The present invention exerts such an effect that almost all diseases can be treated by a simple combination of two or more kinds of drugs which have been previously used.

Since a patient can receive treatment under a condition mild to the patient, the present invention can exert the maximum therapeutic effect while loss of bodily strength of a patient is extremely suppressed, and can avoid an unexpected side effect.

The present invention has large applicability drug industries such as production of drugs for realizing the aforementioned therapy.

What is claimed is:

1. A method for treating transverse colon cancer in a subject in need thereof, said method comprising:
    (a) before performing an operation to remove a tumor from the subject:
        (a1) administering haloperidol orally to the subject at a daily dose of 0.375 mg in a tablet form before bedtime,
        (a2) administering 1200 mg of ascorbic acid and 18 mg of calcium pantothenate to the subject having an empty stomach,
        (a3) upon hospitalization of the subject and when appetite is decreased, infusing 500 ml of an injection solution into the subject, the injection solution containing maltose, potassium chloride, magnesium chloride, potassium hydrogen phosphate, potassium dihydrogen phosphate, sodium chloride, magnesium chloride hexahydrate, anhydrous sodium acetate and maltose monohydrate,
        (a4) orally administering two tablets of 25 mg Luvox containing fluvoxamine maleate to the subject upon a reduction in the subject's blood potassium, and
        (a5) orally administering sodium ferrous citrate to the subject having an empty stomach when the subject has anemia;
    (b) performing an operation to remove as much of the tumor from the subject as possible; and
    (c) beginning at 5 days after the operation and lasting for at least 3 months after the operation:
        (c1) orally administering haloperidol to the subject at a daily dose of 0.375 mg in a tablet form before bedtime,
        (c2) administering 1200 mg of ascorbic acid and 18 mg of calcium pantothenate to the subject having an empty stomach,
        (c3) orally administering two tablets of 25 mg Luvox containing fluvoxamine maleate to the subject upon a reduction in the subject's blood potassium.

2. The method of claim 1, wherein the treatment in step (c) lasts for at least 3 years after the operation.

* * * * *